United States Patent
Danyluk et al.

(10) Patent No.: US 6,717,413 B1
(45) Date of Patent: Apr. 6, 2004

(54) CONTACT POTENTIAL DIFFERENCE IONIZATION DETECTOR

(75) Inventors: Steven Danyluk, Atlanta, GA (US); Anatoly Zharin, Minsk (BY)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 09/553,780

(22) Filed: Apr. 21, 2000

(51) Int. Cl.[7] .................. G01N 27/62; G01N 27/66; G01N 27/00
(52) U.S. Cl. .................. 324/459; 324/464; 324/469; 324/71.1
(58) Field of Search .................. 324/459, 455, 324/456, 457, 458, 464, 465, 679, 765, 470, 72.5, 461, 71.1; 250/282, 286, 287

(56) References Cited

U.S. PATENT DOCUMENTS

| | | | |
|---|---|---|---|
| 2,695,564 A | * 11/1954 | Ohmart | 417/89 |
| 3,319,089 A | * 5/1967 | Debiesse et al. | 376/341 |
| 4,104,619 A | * 8/1978 | Hesler | 340/629 |
| 4,166,974 A | * 9/1979 | Vermeers | 324/679 |
| 4,481,616 A | 11/1984 | Matey | |
| H406 H | * 1/1988 | Wohltjen | 436/153 |
| 5,087,533 A | 2/1992 | Brown | |
| 5,136,247 A | 8/1992 | Hansen | |
| 5,723,980 A | 3/1998 | Haase et al. | |
| 5,773,989 A | * 6/1998 | Edelman et al. | 324/765 |
| 5,974,869 A | 11/1999 | Danyluk et al. | |

* cited by examiner

Primary Examiner—Anjan K. Deb
(74) Attorney, Agent, or Firm—Foley & Lardner

(57) ABSTRACT

A nondestructive testing method of condensed matter surfaces, and a sensing device for the measurement of the work function of the surface of a conducting or semiconducting sample. The sensing device includes an ionization chamber, a probe having a first surface, and a potential difference measurement circuit that is capable of measuring a difference in potential between the first surface of the probe and a surface made of another material to be tested. The ionization chamber produces ionized particles that travel out of an output of the ionization chamber and toward the probe. The probe is a non-vibrating probe having a first surface that is either a positively or negatively charged electrode. The measurement circuit of the present invention is capable of sensing the small amount of electrical current that the electrons and ions moving toward the first surface and the testing surface represent.

27 Claims, 8 Drawing Sheets

CONTACT POTENTIAL DIFFERENCE IONIZATION DETECTOR

This invention was made with Government support under Grant Number N00014-95-1-0903 awarded by the Department of the Navy. The Government has certain rights in the invention.

BACKGROUND OF THE INVENTION

1. Field of the Invention

The present invention relates to a contact potential difference ionization detector and method of using such a detector to detect the work function of a surface, and more specifically to a probe for detecting chemical changes on surfaces.

2. Description of Related Art

A Kelvin probe is a name given to a type of sensor that measures the difference in work functions between the probe surface and a surface of interest (the testing surface). This measurement is made by vibrating the probe and detecting an electrical signal related to the vibration frequency. The difference in work function between the Kelvin probe surface and the testing surface results in an electric field when the two surfaces are in electrical contact.

The work function of the surface of an electronic conductor is defined as the minimum amount of work required to move an electron from the interior of the conductor to a point just outside the surface (beyond the image charge region). If an electron is moved through the surface region, its energy is influenced by the optical, electric and magnetic characteristics of the region. Hence, the work function is an extremely sensitive indicator of surface conditions and is affected by absorbed or evaporated layers, surface reconstruction, surface charging, oxide layer imperfections, surface and bulk contamination, and other like properties. Thus, work function measurements are known and can be employed for nondestructive evaluation of surfaces of various materials. See, for example U.S. Pat. No. 5,974,869 which is incorporated by reference herein in its entirety.

The traditional Kelvin probe incorporates a flat circular electrode (termed the reference electrode) suspended above and parallel to a stationary electrode (the specimen), thus creating a capacitor. FIGS. 1a–c illustrate various electron energy diagrams for two different conducting materials. FIG. 1a shows the electron energy level diagram for two conducting specimens that are electrically isolated from one another, where $\phi_1$ and $\phi_2$ are the work functions of the materials, and $\epsilon_1$ and $\epsilon_2$ represent their Fermi levels. In this case, the Fermi energies and work functions are referenced to a potential in the space between the two materials.

In FIG. 1b it can be seen that if an electrical contact is made between the two electrodes, their Fermi levels equalize by the flow of charge (in the direction indicated). The reference potential is no longer the space between the materials, but is now referenced to the Fermi levels. Relative to the Fermi energy, there develops a potential gradient, termed the contact potential $V_c$, between the electrodes. The flow of electrons to equilibrate the Fermi levels causes the two surfaces to become equally and oppositely charged.

Referring to FIG. 1c, the inclusion of a variable "backing potential" $V_b$ in the external circuit permits biasing of one electrode with respect to the other. At the unique point where the (average) electric field between the plates vanishes, there is a null output signal. The work function difference between two surfaces can be found by measuring the flow of charge when the two conducting materials are connected (see FIG. 1b). However, this produces a "once only" measurement as the surfaces become charged, and the charge must dissipate before another measurement can be made.

By vibrating one of the electrodes (the probe), as has been suggested by Zisman and adapted by many researchers, a varying capacitance is produced, and defined as:

$$C = Q/V = \epsilon_r \epsilon_0 A/d \quad (1)$$

Where
 C is the capacitance;
 Q is the Charge;
 V is the Potential;
 $\epsilon_0$ is the permittivity of the dielectric (in an air probe the dielectric is air);
 $\epsilon_r$ is the relative dielectric constant;
 A is the surface area of the capacitor; and,
 d is the separation between the plates.

If the vibration is periodic, then a periodic flow of electrons will result to try to keep the Fermi levels of the two surfaces equal. Therefore, as the separation d increases periodically, the capacitance C decreases periodically.

As the probe oscillates relative to the testing surface, the voltage between the probe and the testing surface can be recorded. If the vibration is sinusoidal, then the peak-to-peak output voltage $V_p$ is given by the equation:

$$V_p = (\Delta V) R C_0 \omega \epsilon \sin(\omega t + \phi) \quad (2)$$

Where
 $\Delta V$ represents the voltage between the Kevin probe and the sample;
 R is the resistance of the measuring circuit;
 $C_0$ is the Kelvin probe capacitance;
 $\omega$ is the frequency of vibration;
 $\phi$ is the phase angle; and,
 $\epsilon$ is the modulation index $(d_1/d_0)$ where $d_0$ is the average distance between the sample and the probe tip, and $d_1$ is the amplitude of oscillation of the probe.

Yet, there are several disadvantages with capacitance probes like the Kelvin probe as modified by Zisman. One problem with the modified Kelvin probe is that the charge of the electrodes must be dissipated before another measurement can be made, which limits the speed of operation of the probe. Another limitation of the modified or Kelvin type probe arises when used in a gas environment. Measurement of the potential difference in a gas environment by capacitance probes presents problems of reproducibility because adsorption of gas on a surface can cause significant changes in the work function. Such adsorption affects not only the samples being tested, but also the probe. A change in the work function of the probe is virtually indistinguishable from a change in the work function of the sample. Other kinds of surface-gas interactions, as well as changes in environmental conditions such as relative humidity, also can strongly influence the measurements made by Kelvin type probes and other capacitance probes.

Another serious limitation of Kelvin type probes is the need for vibration of the probe. The amplitude of vibration limits how close the probe can be placed relative to the testing surface. The signal will be related to this spacing; the closer the probe can be positioned, the greater the signal and sensitively. Vibration of the probe also is a severe experimental constraints. It necessitates a power source and system to vibrate the probe, and the design of the geometry of the vibrating system. A sensing device that could overcome the many limitations of conventional Kelvin type probes would be beneficial.

Thus, it can be seen that there is a need for the present invention, an improvement over the conventional capacitance probe, by providing a contact potential difference ionization detector that has no moving parts, yet is sensitive enough so as to be capable of sensing gas currents due to the separation of ionized gases by the differences in chemical potential between two different metals. The present invention is primarily directed to the provision of such a non-vibrating probe and its incorporation in a detector, where the signal is related to an ionized gas in the gap of the probe surfaces.

SUMMARY OF THE INVENTION

Briefly described, in a preferred form, the present invention provides both a nondestructive testing method of condensed matter surfaces, and a sensing device for the measurement of the work function of the surface of a conducting or semiconducting sample. The present invention can be used to make extremely sensitive motion detectors and accelerometers. This methodology also can be applied to ascertain contact potential for selected non-metals to evaluate changes of chemical state at surfaces.

The present contact potential difference ionization detector comprises an ionization chamber, a probe having a first surface, and a potential difference measurement circuit that is capable of measuring a difference in potential between the first surface of the probe and a testing surface.

The ionization chamber produces ionized particles that travel out of an output of the ionization chamber and into the space between the probe and the testing surface. The probe is non-vibrating having a first surface that is either a positively or negatively charged electrode due to the electrical connection between the first surface and testing surface. The measurement circuit of the present invention is capable of sensing the small amount of electrical current that the ions moving toward the first surface and the testing surface represent.

Thus, an object of the invention is to provide an improved contact potential difference ionization detector.

Another object of the present invention is to provide an improved detector that can be used to make extremely sensitive motion detectors and accelerometers.

Yet another object of the present invention is to provide an improved extremely sensitive method of contact potential ionization detection.

These and other objects, features, and advantages of the present invention will be more apparent upon reading the following specification in conjunction with the accompanying drawings.

DETAILED DESCRIPTION OF PREFERRED EMBODIMENTS

Figure 1A:
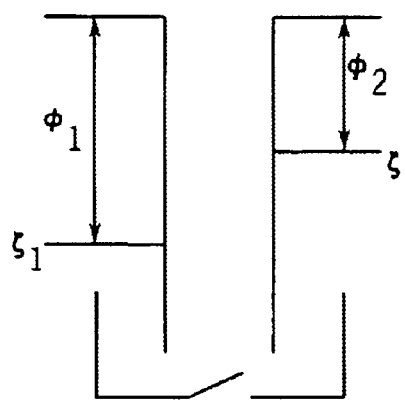
FIG. 1a illustrates an electron energy level diagram for two conducting specimens.
Figure 1B:
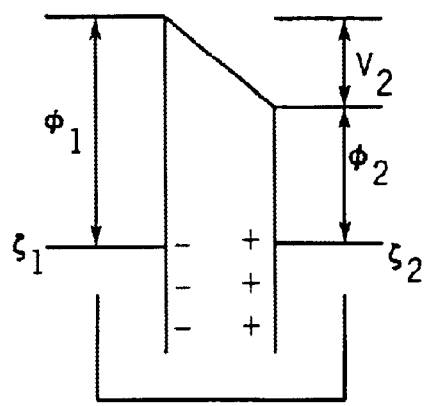
FIG. 1b illustrates the system of FIG. 1a with electrical contact between the two electrodes.
Figure 1C:
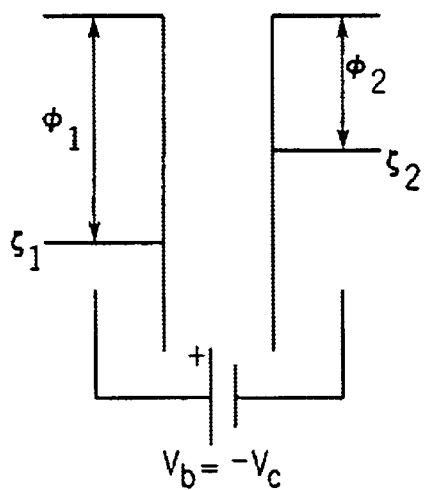
FIG. 1c illustrates the system of FIG. 1b with an added backing potential $V_b$.
Figure 2:
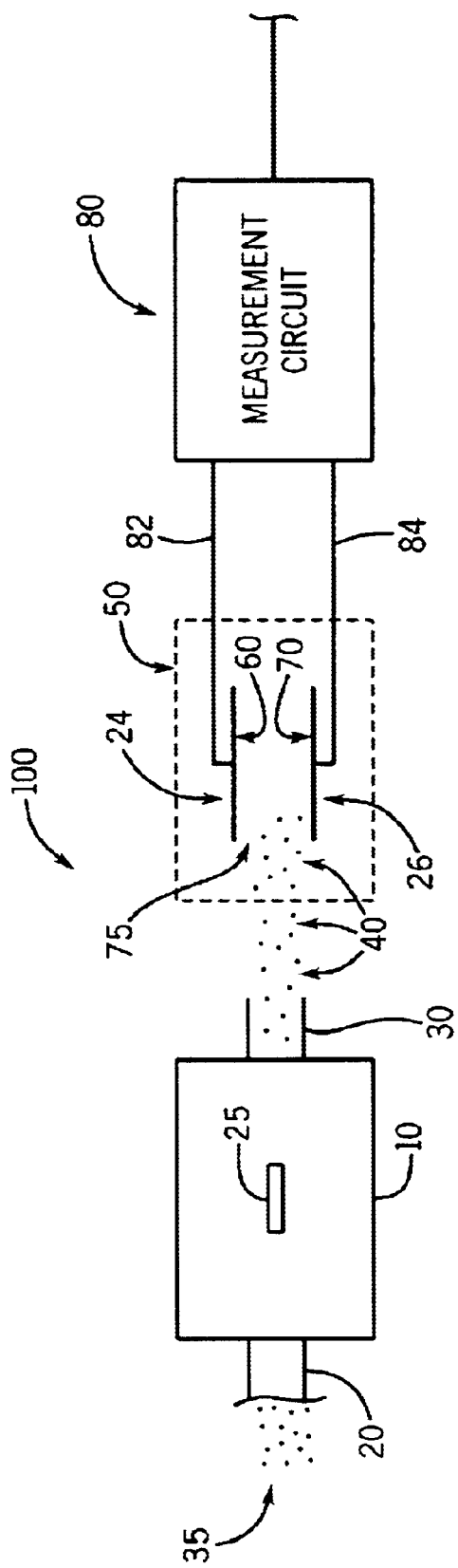
FIG. 2 is a diagram of a contact potential difference ionization detector according to a preferred embodiment of the invention.

Referring now in detail to the figures, wherein like reference numerals represent like parts throughout the several views, FIG. 2 shows a contact potential difference ionization detector 100 (hereinafter, the "detector 100") comprising an ionization chamber 10, a probe 50 having a first surface 60, and a potential difference measurement circuit 80 (hereinafter, the "measurement circuit") that is capable of measuring a difference in potential between the first surface 60 of the probe 50 and a testing surface 70. The testing surface 70 is only a part of the probe 50 as it complements first surface 60 to form a two plate capacitor 75 for the probe 50.

Gas molecules 35 that travel in the environment surrounding the detector 100 enter into an input 20 to the ionization chamber 10 where they become ionized particles 40. The ionized particles 40 then travel out of an output 30 of the ionization chamber 10 and toward the probe 50. In one preferred embodiment of the ionization chamber 10, a source 25 of ionizing radiation for the ionization chamber 10 is an Americium-241 source 87, and in other embodiments can be similar radioactive elements. Preferably, the amount of Americium-241 is approximately 1/5000th of a gram. The radioactive element Americium has a half-life of 432 years, and is a good source of alpha particles for the detector 100.

The probe 50 of the detector 100 comprises a non-vibrating type of probe which includes the first surface 60. The first surface 60 of the probe 50 is part of a positively charged electrode 24, and a negatively charged electrode 26 includes the second surface 70 which is thus a negatively charged surface. However, these charges can be reversed depending on what materials are being used in the probe 50. The probe 50 electrically connects the surfaces 60 and 70 so that the Fermi energies are equal. The charges on the surfaces 60 and 70 occur when the surfaces 60 and 70 are electrically connected and a difference in work functions occurs between them.

Figure 3:
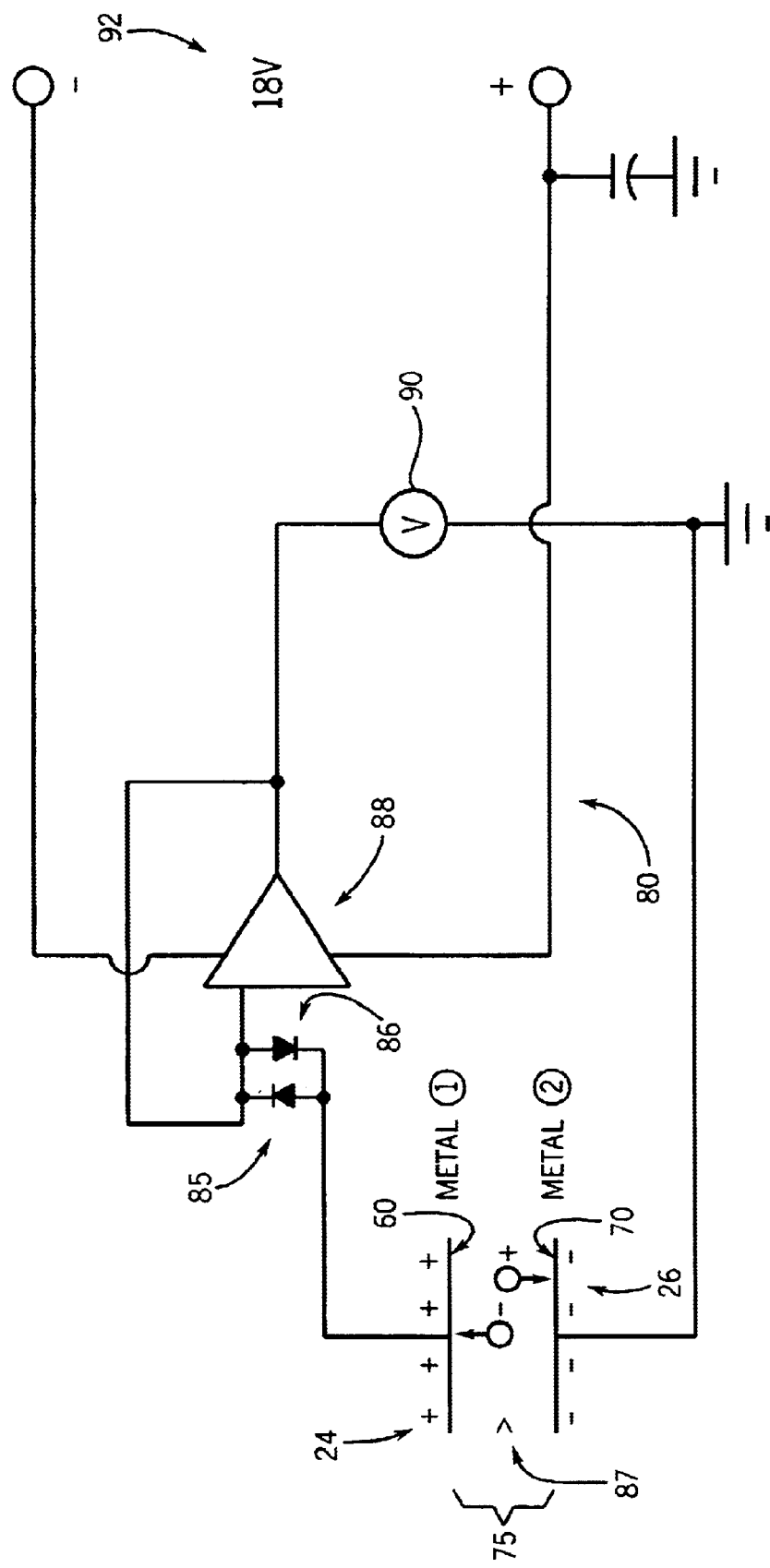
FIG. 3 illustrates a preferred detection circuitry of the present invention.

In one preferred embodiment, the electrode 24 (including the surface 60) is flat, as illustrated in FIG. 3, and the electrodes 24 and 26 (including the respective surfaces 60 and 70) are, respectively, two different conductive materials. Also shown are first diode 85 and second diode 86, along with voltage source 90, amplifier 88 and the 18 V power source 92. The Americium source 87 ionizes the gas between the two surfaces 60 and 70. When the metal electrodes 24 and 26 are connected, the contact potential produces an electrical field between the metal electrode 24 and 26. The electrical field separates the ionized gas and produces a voltage related to the contact potential difference, the number of ionized atoms and the gain of the amplifier 88. The voltage source 90 also enables applying a bias potential to the first surface 60 and the testing surface 70. The voltage output will also be related to the number of gas molecules in the gap (between 60 and 70 in FIG. 3), the rate of ionization of these molecules and the rate at which the molecules strike the surfaces 60 and 70. As air or other gas molecules move into or out of the space between 60 and 70, the voltage will vary if all other parameters are kept constant. If motion occurs outside of the space between 60 and 70, this will cause gas molecules to flow into the space. In this way, the non-vibrating ionization probe can serve as a motion detector. Such a motion detector would be very sensitive since the probe signals are very sensitive to the motion of gas molecules and the number of gas molecules. This probe would be more sensitive than currently available motion detectors. Other applications of this motion detector would involve the building of a housing to encapsulate the probe so that only specific molecules can enter the region 60 and 70. Then the probe could discriminate between molecules. Alternatively, the positively charged electrode 24 (including the surface 60) can vary between numerous sizes and shapes that can be chosen by the user of the detector 100 such that an electric field that can attract and repel the appropriately charged ionized particles can be generated by the positively charged electrode 24 (including the surface 60) and the negatively charged electrode 26 (including the surface 70).

The alpha particles generated by, for example, the Americium source 25 in the ionization chamber 10 ionize oxygen and nitrogen atoms that are constantly entering the input 20 of the ionization chamber 10. Such ionization provides a free electron (with a negative charge) and an atom missing one electron (with a positive charge), namely an ion. The negative electron is attracted to the positive electrode (including the surface 60), while the positively charged atoms are attracted to the negatively charged surface 70.

In a preferred embodiment of the circuit 80 shown in FIG. 3 the measurement circuit 80 of the present detector 100 is capable of sensing the small amount of electrical current embodied in the motion of these electrons and ions moving toward the surfaces 60 and 70. One important feature of the present detector 100 is the sensing of signals from the non-vibrating probe 50, wherein the signal is related to an ionized gas present in the gap between the two surfaces 60 and 70. An extremely sensitive method of contact potential ionization detection according to the present invention comprises the steps of generating an electric field between the surfaces 60 and 70 of the probe 50 and measuring the current using the measurement circuit 80. The electric field is characteristic of the contact potential difference. If the gas that exists between the surfaces 60 and 70 is ionized, then the contact potential difference, or electric field, attracts the ionized gas. When the gas strikes the surface of the appropriate electrode 24 and 26 (including the respective surfaces 60 and 70), a current in the measurement circuit 80 is recorded. Thus, there is no need to vibrate one of the electrodes 24 and 26. The current is then related to the ionization source and the value of the contact potential difference, or the electrical field between the surfaces 60 and 70.

In yet another form of the invention the probe 50 can be used advantageously as a motion detector. The probe 50 operates in the manner described hereinbefore but the output signal from the measurement circuit 80 is characteristic not only of contact potential difference between the two surfaces 60 and 70 but also a function of motion of the molecules 35 input to the ionization chamber 10 and the resulting ions 40 attracted to the surfaces 60 and 70. The voltage output will be related to the number of gas molecules in the gap (between 60 and 70 in FIG. 3), the rate of ionization of these molecules and the rate at which the molecules strike the surfaces 60 and 70. As air or other gas molecules move into or out of the space between 60 and 70, the voltage will vary if all other parameters are kept constant. If motion occurs outside of the space between 60 and 70, this will cause gas molecules to flow into the space. In this way, the non-vibrating ionization probe can serve as a motion detector. Such a motion detector would be very sensitive since the probe signals are very sensitive to the motion of gas molecules and the number of gas molecules. This probe would be more sensitive than currently available motion detectors. Other applications of this motion detector would involve the building of a housing to encapsulate the probe so that only specific molecules can enter the region 60 and 70. Then the probe could discriminate between molecules.

The following non-limiting examples provide examples of various embodiments of the invention.

Example I

Figure 4:
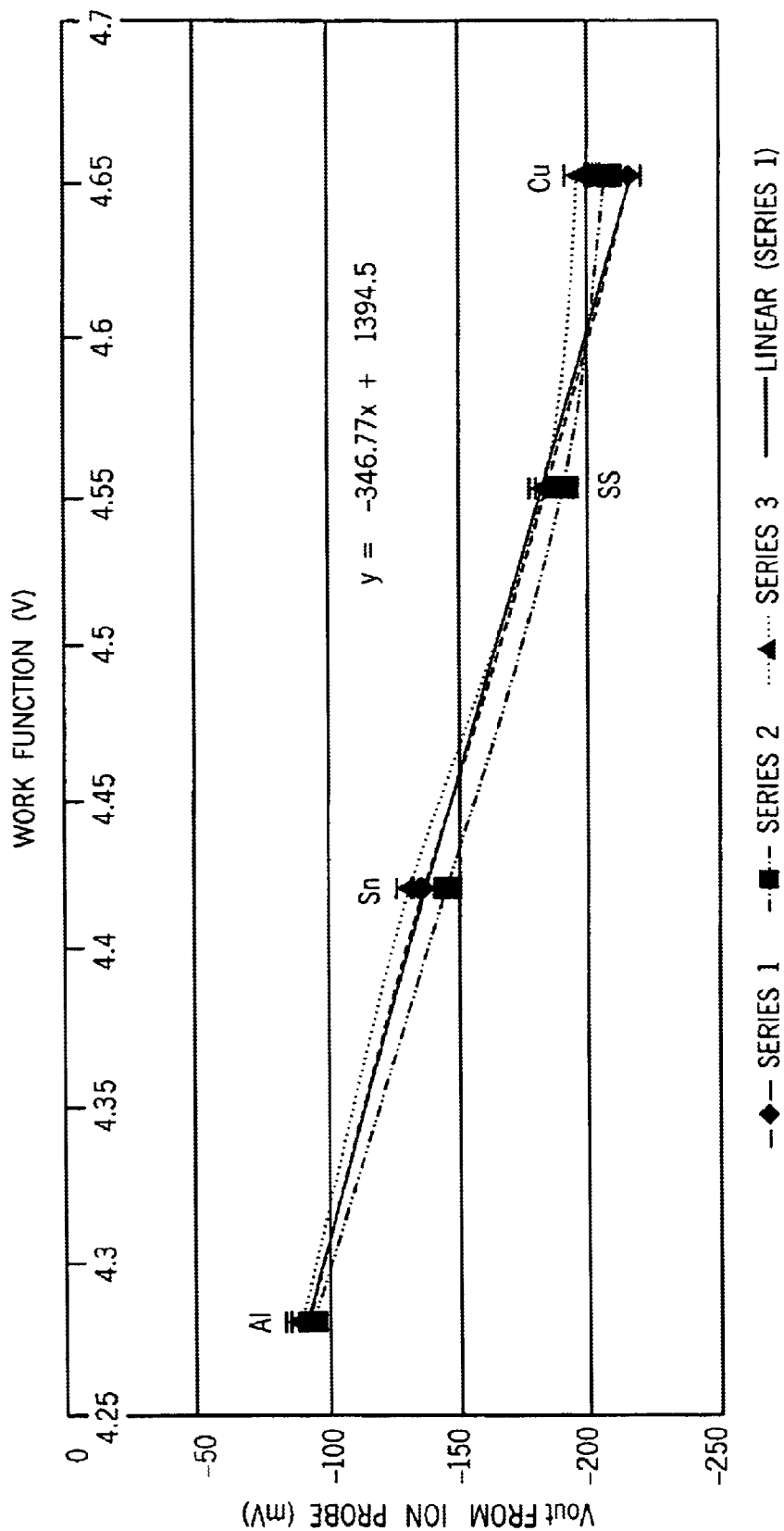
FIG. 4 shows ion probe voltage values versus work function values for a series of metals.

Measurement of the Surface Potential of Unknown Metals or Metals That Have Corroded or Otherwise Undergo Changes of Surface Potential This example demonstrates how the voltage output of the ionization probe can be used to determine the work function of metals whose value is not known, or whose value has been changed by corrosion or other surface modification. This can be done as follows: the voltage output of the ionization probe is calibrated against the work functions of selected materials, such as aluminum, copper and tin. The surface of each metal was polished with an abrasive paper (grit size 2400) and the values of the voltage and the known values of the work function are given in the Table below, and these are plotted in FIG. 4.

TABLE

Ionization probe voltage output and work function of three example metals.

| Material | $V_{output}$(mV.) | $\phi$ work function, (V) |
| --- | --- | --- |
| Copper | 180–185 | 4.65 |
| Aluminum | 97–101 | 4.28 |
| Tin | 112–118 | 4.42 |
| Stainless steel | 167–172 | 4.5 (deduced from the graph) |

In addition to these three metals, a fourth sample of stainless steel was also polished in the same way. The voltage for the stainless steel was 167–172 V; and the work function, although unknown, can be deduced to be 4.5 V. In the same way, the work function of other metals and semiconductors can be found from this calibration curve. In addition, if the metal can be exposed to a lubricant, or some other atmosphere, where the surface chemistry is changed, work function will become unknown but can also be obtained. This will also be true if the surface of the unknown metal, semiconductor or other material is corroded or otherwise chemically changed.

Example II

Use of the Ionization Probe as a Gas Flow Meter

Figure 5:
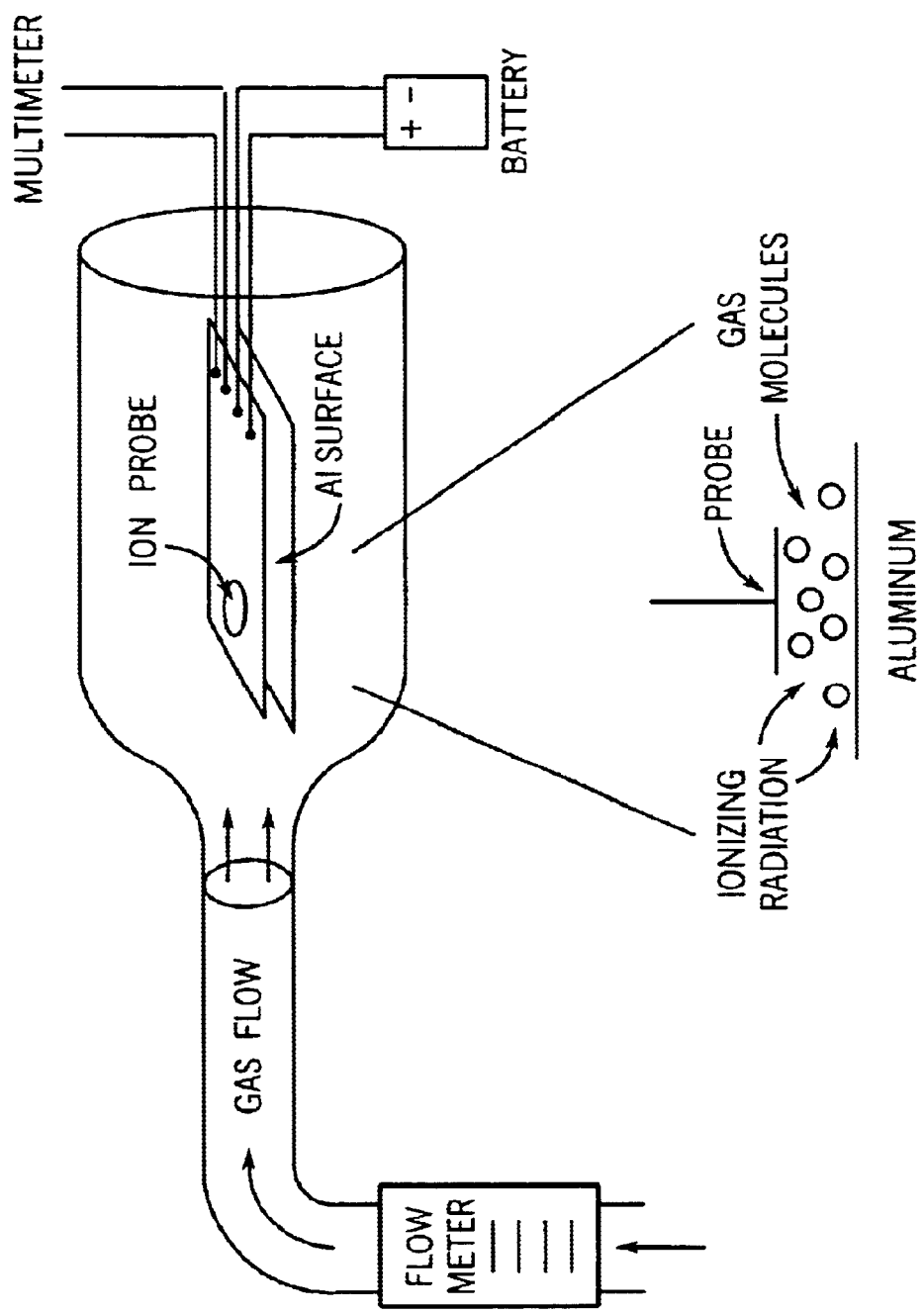
FIG. 5 shows a schematic of apparatus for measurement of ionization probe output arising from gas flow rate.
Figure 6:
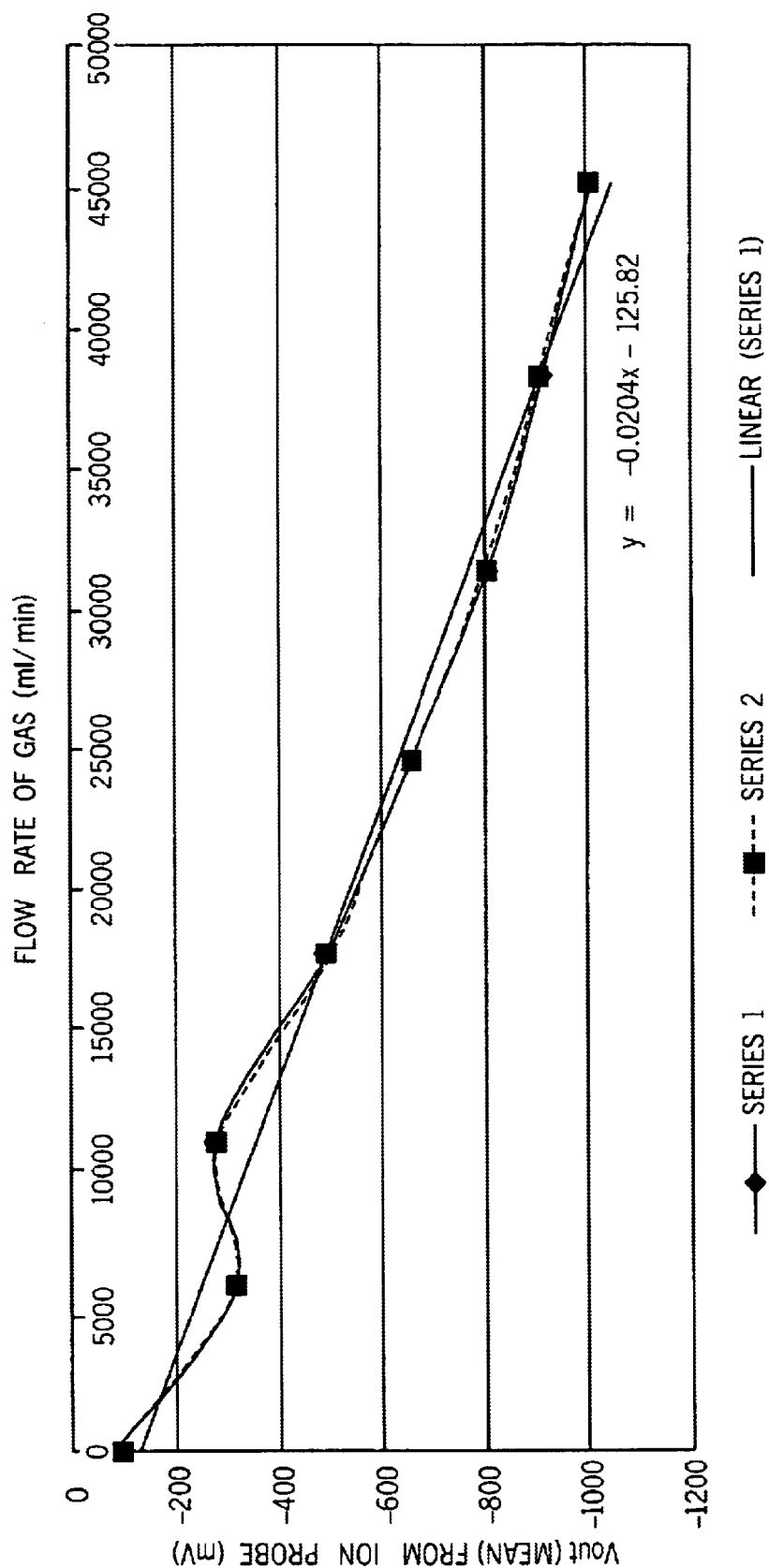
FIG. 6 shows a plot of measured ion probe voltage versus gas flow rate.

The ionization probe can further function as a sensitive gas flow meter. With the probe situated above a metal with a known work function (aluminum, for example) the voltage produced by the circuit will be related to the ionized gas in the gap between the probe and this metal (schematic of apparatus shown in FIG. 5). If the gas in the gap undergoes movement, then the voltage of the ion probe will change. The voltage is then a measure of the movement of the gas molecules in the gap. The sensitivity of the output voltage to gas movement was measured by an experiment where a gas flow was purposely produced, and the output voltage was measured as a function of the flow rate. The ionization probe was inserted into a glass tube, one end of which was connected to a dry air gas cylinder. A calibrated flow meter was used to measure the flow of the gas. The measurements of the ion probe voltage (V) and the gas flow rate (ml/min) is shown in FIG. 6. This plot shows that the flow rate can be deduced from measurements of the voltage.

Example III

Ion Probe used as an Accelerometer

Figure 7:
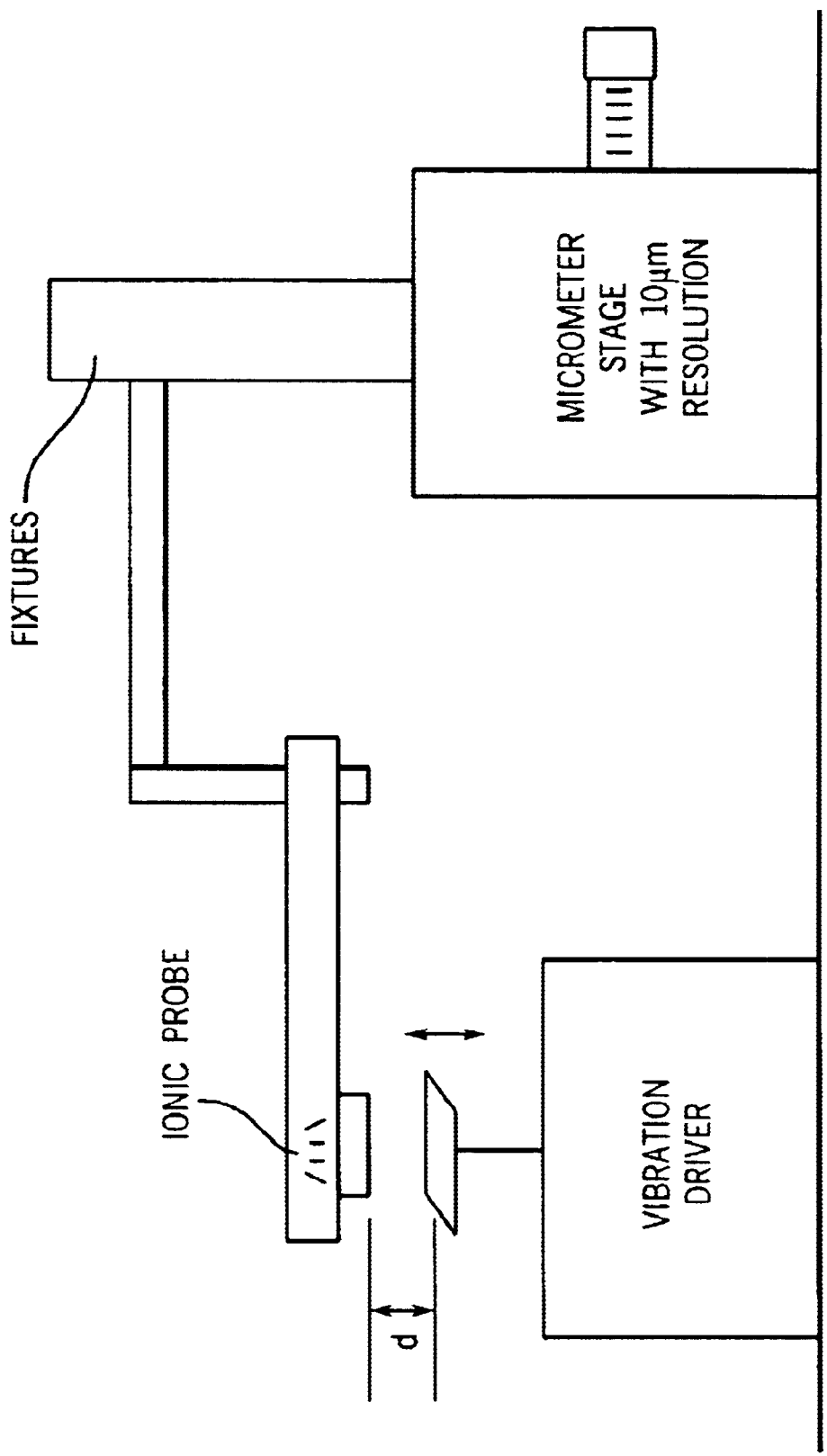
FIG. 7 shows a schematic diagram of the probe used to measure surface vibration.
Figure 8:
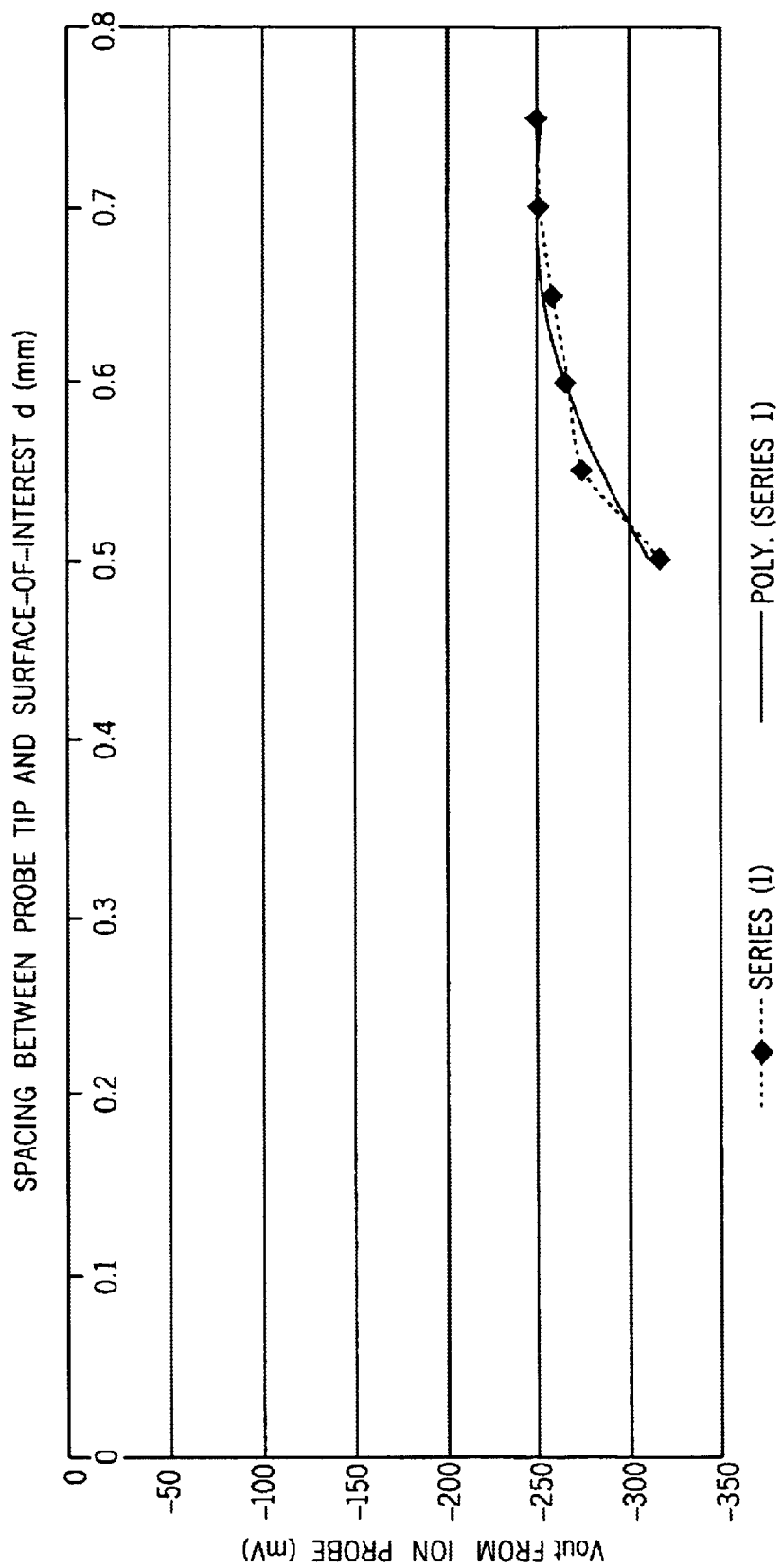
FIG. 8 shows a plot of ionization probe output voltage versus spacing between the tip of the probe and a vibrating surface.

The ion probe can also be used as an accelerometer. By arrangement of an experiment as shown in FIG. 7 the ion probe is positioned above a surface whose spacing, d, and amplitude of vibration can be measured and controlled. In these experiments the voltage output of the probe can be demonstrated to be related to d, the spacing. FIG. 8 shows the voltage (V) versus spacing (mm) for six spacings ranging from 0.5 to 0.75 mm. As can be seen in this figure there is a reciprocal relationship between the voltage output and the spacing.

While the invention has been disclosed in its preferred forms, it will be apparent to those skilled in the art that many modifications, additions, and deletions can be made therein without departing from the spirit and scope of the invention and its equivalents, as set forth in the following claims.

What is claimed is:

1. A detector capable of detecting the work function of a testing surface, said detector comprising:
    a probe having a first surface, said probe having a testing position wherein said first surface is positionable proximate to the testing surface, said probe in the testing position being capable of producing an electric field between said first surface and the testing surface;
    an ionization source of ionized particles, said ionization source having an ionization source output, said ionization source arranged such that a portion of the ionized particles exit said ionization source output and are capable of being influenced by an electric field generated at said first surface of said probe; and
    a potential difference measurement circuit capable of measuring a difference in potential between said first surface and the testing surface when said probe is in the testing position.

2. The detector of claim 1, said first surface being a first conductive material.

3. The detector of claim 2, said first conductive material being different than material of the testing surface.

4. The detector of claim 1, said first surface being maintained at a fixed distance from the testing surface when said probe is in the testing position.

5. The detector of claim 1, said potential difference measurement circuit comprising a power supply circuit that is capable of supplying a first bias potential to said first surface.

6. The detector of claim 5, said power supply circuit capable of maintaining the testing surface at a testing bias potential approximately equal to ground.

7. The detector of claim 1, said potential difference measurement circuit comprising:
    a comparator including a first comparator input, a second comparator input and comparator output, said first comparator input capable of receiving a signal indicative of a first bias potential at said first surface, said second comparator input capable of receiving a signal indicative of a testing bias potential at said testing surface, said comparator output capable of generating a signal indicative of the difference between the signals indicative of said first bias potential and said testing bias potential;
    a first diode including a first diode anode and a first diode cathode, said first diode anode coupled to said first comparator input and said first diode cathode coupled to said second comparator input; and,
    a second diode including a second diode anode and a second diode cathode, said second diode anode coupled to said second comparator input and said second diode cathode coupled to said first comparator input.

8. The detector of claim 1, said probe being a non-vibrating probe.

9. A detector capable of detecting measurements reflective of the work function of a testing surface, said detector comprising:
    a non-vibrating probe having a first conductive material, said probe having a testing position wherein said first conductive material is positionable proximate to the testing surface, said probe in the testing position being capable of producing an electric field between said first conductive material and the testing surface;
    an ionization source of ionized particles, said ionization source having an ionization source output and said ionization source arranged such that a portion of the ionized particles exit said ionization source output and are capable of being influenced by an electric field generated at said first conductive material of said probe; and
    potential difference measurement circuit capable of measuring a difference in potential between said first conductive material and the testing surface when said probe is in the testing position, said potential difference measurement circuit including a power supply circuit capable of supplying a first bias potential to said first conductive material.

10. The detector of claim 9, said first conductive material being maintained at a fixed distance from the testing surface when said probe is in the testing position.

11. The detector of claim 9, said power supply circuit capable of maintaining the testing surface at a testing bias potential approximately equal to ground.

12. The detector of claim 9, said first conductive material being a material different than the testing surface.

13. The detector of claim 9 wherein said first conductive material is selected from the group consisting of an insulator, an ionic material, a semiconductor and a covalent material.

14. A potential difference detector comprising:
    a non-vibrating probe having a first surface and a second surface, said first surface being a first conductive material and said second surface being a second conductive material;
    a measurement device capable of measuring the potential difference of said non-vibrating probe when said probe is provided with ionized gas particles; and
    an ionization source of ionized particles, said ionization source being capable of providing ionized gas particles to said non-vibrating probe.

15. The potential difference detector of claim 14, said measurement device including a biasing element, said biasing element being capable of providing a bias potential to said non-vibrating probe.

16. The potential difference detector of claim 14, said first conductive material being different than said second conductive material.

17. A motion detector comprising:

a first conductive element for operating at a first bias potential;

a second conductive element for operating at a second bias potential;

an ionization source having an ionization source input and an ionization source output, said ionization source input for receiving gas molecules, said ionization source output capable of providing ionized gas molecules to said first conductive element and said second conductive element; and a potential difference measurement circuit having a first potential difference input, a second potential difference input and a potential difference output, said first potential difference input capable of receiving a signal indicative of the first bias potential, said second potential difference input capable of receiving a signal indicative of the second bias potential, said potential difference output generating an output signal indicative of the difference between the signals indicative of said first bias potential and said second bias potential, said output signal being a function of motion of the gas molecules in said motion detector.

18. The motion detector of claim 17, said potential difference measurement circuit comprising:

an amplifier having a first amplifier input, a second amplifier input and an amplifier output, said first amplifier input coupled to one of said conductive elements, said second amplifier input coupled to the other of said conductive elements; and a voltage source coupled to said amplifier output and said first amplifier input.

19. The motion detector of claim 17, said first conductive element and said second conductive element being maintained at a fixed distance with respect to one another.

20. A method of detecting the work function of a testing surface, said method comprising the following steps:

forming ionized particles;

directing said ionized particles toward a probe having a first surface being in proximity to the testing surface;

generating an electric field between said first surface and the testing surface; and measuring a difference in potential between said first surface and the testing surface.

21. The method of detecting the work function according to claim 20, said step of forming ionized particles being provided by an ionization source, said ionization source having an ionization source input and an ionization source output.

22. The method of detecting the work function according to claim 21, said step of directing said ionized particles being provided by said ionization source arranged such that a portion of the ionized particles exit said ionization source output and are capable of being influenced by the step of generating the electric field.

23. The method of detecting the work function according to claim 20, said step of measuring a difference in potential being provided by a potential difference measurement circuit.

24. The method of detecting the work function according to claim 23, said potential difference measurement circuit comprising a power supply circuit that is capable of supplying a first bias potential to said first surface.

25. The method of detecting the work function according to claim 24, said power supply circuit capable of maintaining the testing surface at a testing bias potential approximately equal to ground.

26. The method of detecting the work function according to claim 20, further comprising a step of maintaining said first surface at a fixed distance from the testing surface.

27. The method of detecting the work function according to claim 20, said probe being a non-vibrating probe.

* * * * *